United States Patent [19]

Schacht et al.

[11] Patent Number: 4,965,397
[45] Date of Patent: Oct. 23, 1990

[54] NOVEL DIBASIC ACID SALTS AND THEIR SYNTHESIS

[75] Inventors: Etienne Schacht, Staden; Jan Crommen, Gent, both of Belgium

[73] Assignee: Ethyl Corporation, Richmond, Va.

[21] Appl. No.: 298,921

[22] Filed: Jan. 23, 1989

[51] Int. Cl.$^5$ .............................. C07C 101/18
[52] U.S. Cl. ...................... 560/60; 560/38; 560/145; 560/155; 528/321
[58] Field of Search ............ 560/38, 155, 60, 145

[56] References Cited
PUBLICATIONS

Gibian, Chem. Abst. 55:27114i–27116g (1961).

*Primary Examiner*—Michael L. Shippen
*Attorney, Agent, or Firm*—John F. Sieberth; Richard J. Hammond

[57] ABSTRACT

The protecting group, Z, of protected alpha-amino acid esters of the formula $$Z-NH-CH(R_2)COOCH(R)COOR_1$$

is removed in the presence of a dibasic acid such as oxalic acid. This results in the formation of a new type of salt of an amino acid ester which may be represented by the formula $$Q_p(COO^-)_2(H_3\overset{+}{N}CH(R_2)COOCH(R)COOR_1)_2$$

In the above Q is a divalent hydrocarbyl residue of a dibasic acid, R is a hydrogen atom or hydrocarbyl group, $R_1$ is a hydrocarbyl group, $R_2$ is a hydrogen atom or hydrocarbyl group, and p is zero or one, preferably zero. When p is zero, the salts are oxalate salts. When p is one, the salts are salts of other dibasic acids. The salts (II) are useful as reactants in the synthesis of amino-acid substituted phosphazene polymers.

14 Claims, No Drawings

NOVEL DIBASIC ACID SALTS AND THEIR SYNTHESIS

TECHNICAL FIELD

This invention relates to a new class of dibasic acid salts and methods for their production.

THE INVENTION

This invention involves, inter alia, the discovery of a new class of dibasic acid salts of amino acids and a method by which they may be prepared.

By reacting a protected alpha-amino acid or salt thereof with an alpha-haloalkanoic acid ester in a liquid reaction solvent and in the presence of a tertiary amine, alkylation of the protected alpha-amino acid occurs. The resultant amino acid ester may be represented by the formula

$$Z-NH-CH(R_2)COOCH(R)COOR_1 \quad (I)$$

wherein Z is the protecting group, $NH-CH(R_2)CO$ is the residue of the alpha-amino acid, $R_1$ is a hydrocarbyl group, and each of R and $R_2$ is independently a hydrogen atom or a hydrocarbyl group.

When pursuant to this invention the protecting group is removed in the presence of a dibasic acid such as oxalic acid, a new type of salt is produced. Such salts may be represented by the formula

$$Q_p(COO^-)_2(H_3\overset{+}{N}CH(R_2)COOCH(R)COOR_1)_2 \quad (II)$$

wherein Q is a divalent hydrocarbyl residue of a dibasic acid, R is a hydrogen atom or hydrocarbyl group, $R_1$ is a hydrocarbyl group, $R_2$ is a hydrogen atom or hydrocarbyl group, and p is zero or one, preferably zero. When p is zero, the salts are oxalate salts. When p is one, the salts are salts of other dibasic acids, such as malonates, succinates, glutarates, phthalates and the like. One preferred group of such salts are those in which $R_2$ is a hydrogen atom.

The salts of formula (II) are particularly useful as reactants in the synthesis of amino-acid substituted polyphosphazene polymers. For example by reacting the amino acid ester salts with a dihalophosphazene polymer in a liquid reaction solvent and in the presence of a hydrogen halide acceptor, partial substitution of the halogen of the dihalophosphazene polymer by amino acid ester groups occurs, thereby forming a partially substituted polymer. On reacting the partially substituted polymer with a glycine ester in a liquid reaction solvent and in the presence of a hydrogen halide acceptor the remaining halogen of the partially substituted polymer can be replaced by glycine ester groups to thereby form an essentially halogen-free substituted polymer. Such polymers have a controllable set of properties including hydrolytic stability, permeability, hydrophobicity and bioacceptability, and thus can be tailored within limits to provide release characteristics rendering them suitable for use in the production of biomedical implants and other drug release systems. In addition, these polymers may be used for manufacture of a variety of other biocompatible objects such as sutures and the like.

To form the esters of formula (I) above, any suitable protected alpha-amino acid or salt thereof may be reacted with any suitable alpha-haloalkanoic acid ester. Typical protected alpha-amino acids which may be used in this reaction include glycine, alanine, leucine, phenylalanine, or the like in which the amino group is protected by a suitable protecting group. Among the protecting groups that may be considered for use are:

(a) Amine protecting groups which can be removed by catalytic hydrogenation or similar reduction techniques, including (1) urethane protecting groups derived from primary alcohols
  benzyloxycarbonyl groups with (multiple) substituents in the aromatic ring
  5-benzisoxazolymethyleneoxycarbonyl group
  fluorenylmethyloxycarbonyl group
  pyridine-4-methyloxycarbonyl group
(2) urethane protecting groups derived from secondary alcohols
  diphenylmethyloxycarbonyl group and its pyridine analogue
(3) urethane protecting groups derived from tertiary alcohols
  2-(4-pyridyl)propyl-2-oxycarbonyl
  N,N-dimethylaminoethyldiphenylmethoxycarbonyl
  2-(N,N-dimethylcarbamoylethyl)propyl-2-oxycarbonyl
(4) alkyl protecting groups
  triphenylmethyl group (b) Amine protecting groups which can be removed fast at room temperature in non-aqueous HX-AcOH mixtures, including (1) urethane protecting groups derived from secondary alcohols
  cyclopentyloxycarbonyl group
  cis-2-methylcyclohexyloxycarbonyl
(2) urethane protecting groups derived from tertiary alcohols
  t-butyloxycarbonyl group
  adamantyloxycarbonyl group
  t-butyloxy derivatives with a methyl group substituted by an aromatic residue or the like. While the free protected amino acid may be used, it is preferably converted in situ to a suitable salt, such as a sodium, potassium or ammonium salt. Crown ethers or like materials may be added to promote dissociation of the salt. Among the numerous alpha-haloalkanoic acid esters which may be employed in this reaction are the alkyl, alkenyl, cycloalkyl, aryl and aralkyl esters of the alpha-chloro and alpha-bromoalkanoic acids, such as methyl 2-chloroacetate, methyl 2-bromoacetate, ethyl 2-chloroacetate, ethyl 2-bromoacetate, propyl 2-chloroacetate, butyl 2-bromoacetate, hexyl 2-chloroacetate, octyl 2-bromoacetate, cyclopentyl 2-chloroacetate, cyclohexyl 2-bromoacetate, cyclopropylcarbinyl 2-chloroacetate, phenyl 2-bromoacetate, 4-ethylphenyl 2-chloroacetate, benzyl 2-bromoacetate, 2-phenethyl 2-chloroacetate, allyl 2-bromoacetate, and like esters of such acids as propionic, butyric, valeric, hexanoic, octanoic and decanoic acids, and the like. Use of lower alkyl esters (e.g., $C_1-C_6$), especially the ethyl esters, is preferred. Esters of alkanoic acids having a leaving group other than halide in the alpha position (e.g., $+N_2-$, -OTos, -OMes, etc.) may also be used.

The reaction may be conducted in any of a variety of solvents such as methyl acetate, ethyl acetate, butyl acetate, acetonitrile, N,N-dimethylformamide, N,N-dimethylacetamide, dimethylsulfoxide, and the like.

Hydrogen halide acceptors that may be utilized in this reaction include tertiary amines such as trimethylamine, triethylamine, tripropylamine, tributylamine, trihexylamine, tetramethylethylene diamine, pyridine, 1,4-diazabicyclo[2.2.2]octane, N-methylpyrrole, N-methylmorpholine, and the like. The amount used can vary from 1 to several equivalents relative to the amount of protected amino acid or salt, although one equivalent gives satisfactory results.

Relatively mild reaction conditions are generally employed, with temperatures in the range of about 20 to about 125° C being typical.

This reaction can also be achieved with either the potassium salt or the dicyclohexylamine salt of the protected amino acid in N,N-dimethylformamide or dimethylsulfoxide, with NaI as a catalyst and at room temperature.

To remove the protecting group from the product of formula (I), various procedures may be used depending upon the type of protecting group being utilized. With groups such as the carbobenzyloxycarbonyl protecting group catalytic hydrogenation in an alcoholic medium in the presence of oxalic acid has been found particularly efficacious. Amounts of oxalic acid ranging from 1 to 3 equivalents, pressures ranging from atmospheric up to 30 psi, and use of various alcoholic media (methanol, ethanol, propanol, isopropanol, butanol, etc.) provide satisfactory results. Temperatures should however be kept below about 40° C, as temperatures higher than this tend to promote intense decomposition of the reaction product.

Other methods which may be found suitable, under appropriate circumstances, for removing the Z-group include use of:

(1) Cyclohexene and Pd/C or Pd/CaCO$_3$ in dry EtOH (2) Cyclohexadiene and Pd/C or Pd/CaCO$_3$ in dry EtOH (25° C)

(3) Ammonium formate and Pd/C in dry EtOH (0°–40° C)

The practice of this invention is illustrated by the following examples.

EXAMPLE 1

Synthesis of Protected Ethyl 2-(0-glycyl)lactate Z-glycine (Z=carbobenzyloxycarbonyl) was prepared by standard procedures discussed in Boissonnas et al, *Helv. Chim. Acta*, 1953, Vol. 36, pages 875 et seq. 19.9 Grams (0.11 mole) of ethyl 2-bromopropionate was added dropwise to a solution of 20.1 g (0.1 mole) of Z-glycine and 10.1 g (0.1 mole) of triethylamine in 150 mL of ethyl acetate. The reaction mixture was stirred at reflux for 48 hr. After removal of the insoluble hydrobromide salt by filtration, the mixture was washed with dilute HCl and NaHCO$_3$ solution and with water. After drying with Na$_2$SO$_4$, the organic phase was evaporated to a colorless viscous oil. Ethyl Z-amino-2-(O-glycyl)lactate (28.5 g, 0.092 mole, yield =92%) was isolated by adsorption chromatography on silica gel (EtOAc/Hexane 1:1 (v/v).

Ethyl Z-amino-2-(O-alanyl)lactate can be made in the same manner as in Example 1 using an equivalent quantity of Z-alanine in lieu of Z-glycine. L-, D-, and DL-alanine can be used in these preparations.

EXAMPLE 2

Synthesis of Protected Ethyl 2-(0-glycyl)glycolate 25.2 g ethyl 2-bromoacetate (0.15 mole, d=1.5 g/mL) was added dropwise to a solution of 20.1 g Z-glycine (0.1 mole) and 10.1 g triethylamine (0.1 mole, d=0.729 g/mL) in 150 mL ethylacetate. The reaction mixture was stirred at reflux during 2 hours. After removal of the insoluble hydrobromide salt, the mixture was washed with diluted HCl, NaHCO$_3$ solution and finally with water. After drying over Na$_2$SO$_4$ the organic layer was evaporated to a viscous oil. Ethyl Z-amino-2-(O-glycyl)glycolate (18.4 g, 0.062 mole, yield =62%) was isolated by crystallization in n-pentane.

EXAMPLE 3

Removal of the Z-Group from Protected Ethyl 2-(0-glycyl)lactate

A solution of 5 g ethyl Z-amino-2-(O-glycyl)lactate and 1.07 g oxalic acid in 500 mL super dry ethanol was hydrogenated in a Parr Reductor apparatus in presence of 1 g Pd/C catalyst, (hydrogen pressure was 30 psi, temperature was 30°–35° C). When hydrogen pressure remained constant (ca. 2 h) the Pd/C catalyst was removed immediately from the warm reaction mixture by filtration. The filtrate was allowed to cool to 0° C overnight. This resulted in the formation of ethyl 2-(0-glycyl)lactate ammonium oxalate•crystals which was isolated by filtration and drying under vacuum.

The same procedure was used in removing the protective group from ethyl Z-amino-2-(O-glycyl)glycolate thereby forming ethyl 2-(0-glycyl)glycolate in an isolated yield of 90%. Ethyl 2-(0-alanyl)lactate ammonium oxalate was also produced in the same manner from Z-amino-2-(O-alanyl)lactate.

Example 4 illustrates how the compounds of this invention may be used in making novel phosphazene polymers.

EXAMPLE 4

Synthesis of [NP(NHCH(CH)COOCH(CH$_3$)COOEt)$_{2x}$(GlyOEt)$_{2y}$y]$_n$

In this synthesis procedure all reactions were carried out under an atmosphere of dry nitrogen and contact with the atmosphere during filtrations was kept to a minimum. To a suspension of dried ethyl 2-(0-alanyl)-lactate ammonium oxalate (3.4 g; 0.0145 mole -NH$_3^+$) in 75 mL very dry acetonitrile was added 2.02 mL (90.0145 mole) dry and purified triethylamine. The mixture was then stirred for a few minutes until a clear solution was obtained. This solution was then added dropwise to an excess of dry THF (200 mL). After removal of the insoluble oxalate salt by filtration, respectively 165, 77, 33 and 0 mL of the filtrate (containing respectively 0.0087; 0.0046; 0.00174; 0.00 mole ethyl 2-(0-alanyl)lactate were each transferred into a separate 500 mL flask, each diluted with dry THF to a total volume of 165 mL. These mixtures were then cooled to 0° C as dry purified triethylamine (respectively 1.19; 0.57; 0.24; and 0 mL) was added. To each of these reaction mixtures a solution of 1 g (NPCl$_2$)$_n$ (8.75 mL 11.4% solution in cyclohexane) in 80 mL dry THF was added dropwise. Stirring was continued for 19 hours. Meanwhile dried glycine ethyl ester hydrochloride (19.25 g) was transferred into a 500 mL flask containing dry THF (240 mL), and 19.1 mL dry, purified triethylamine. This mixture was stirred and refluxed for 3.5 hours followed by removal of insoluble HCl-salts by filtration at room temperature. When reaction of ethyl 2-(0-alanyl)lactate with (NPCl$_2$)$_n$ was completed, the prepared glycine ethyl ester solution was divided into four equal parts (60 mL) and each part is added to one of the reaction mixtures at 0° C together with dry, purified triethylamine (respectively 1.19; 1.18; 2.15; and 2.4 mL). The reaction mixtures were then stirred for an additional 19 hours. After removal of the insoluble HCl-salts by filtration, the polymer solution was concentrated by vacuum evaporation of solvent at 30-35° C Addition of the resultant viscous polymer solutions to 300 mL dry n-heptane while stirring yielded a polymer gel. Reprecipitation from dry chloroform into 300 mL n-heptane and again into 300 mL dry diethyl ether yielded a white solid polymer poly(ethyl 2-(O-glycyl lactate)co(ethyl glycinate)phosphazene free of HCl-salts. The values of x and y in the three polymer samples so produced (as determined by $^1$H-NMR) were (1) x=0.30, y=0.70; (2) x=0.10, y=0.90; (3) x=0.05, y=0.95.

A similar procedure to that of Example 4 was used to produce three samples of poly(ethyl 0-glycyl-2-lactate)-co(ethyl glycinate)phosphazene:

These three polymer samples gave the following values for x and y: (1) x=0.45, y=0.55; (2) x=0.25, y=0.75; (3) x=0.10, y=0.90.

Conventional methods are applicable for transforming the polymers into suitable shapes for use as body implants, and into filaments for use as sutures. The polymers may also be used for forming plaques, sheets, and other molded objects.

The foregoing disclosure has been presented for purposes of illustration and not limitation. As can readily be appreciated by those skilled in the art, this invention is susceptible to considerable variation in its practice within the spirit and scope of the ensuing claims.

We claim:
1. A compound of the general formula

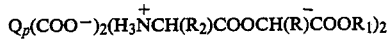

wherein Q is the divalent hydrocarbyl residue of a dibasic acid, R is a hydrogen atom or hydrocarbyl group, $R_1$ is a hydrocarbyl group, $R_2$ is a hydrogen atom or hydrocarbyl group, and p is zero or one.

2. A compound of claim 1 wherein p is zero.
3. A compound of claim 1 wherein R is a hydrogen atom.
4. A compound of claim 3 wherein p is zero.
5. A compound of claim 3 wherein R is a hydrogen atom.
6. A compound of claim 3 wherein R is a methyl group.
7. A compound of claim 3 wherein R is an isopropyl group.
8. A compound of claim 3 wherein R is an isobutyl group.
9. A compound of claim 3 wherein R is an n-butyl group.
10. A compound of claim 3 wherein R is a sec-butyl group.
11. A compound of claim 3 wherein R is a benzyl group.
12. Ethyl 2-(0-glycyl)glycolate ammonium oxalate, a compound of claim 1.
13. Ethyl 2-(O-glycyl) lactate ammonium oxalate, a compound of claim 1.
14. Ethyl 2-(O-alanyl) lactate ammonium oxalate, a compound of claim 1.

* * * * *

UNITED STATES PATENT AND TRADEMARK OFFICE
CERTIFICATE OF CORRECTION

PATENT NO.   :   4,965,397
DATED        :   October 23, 1990
INVENTOR(S)  :   Etienne Schacht It is certified that error appears in the above-identified patent and that said Letters Patent is hereby corrected as shown below:

On the title page:
  In the Abstract, line 9 reads "In the above Q is a divalent" and should read -- In the above formulas Q is a divalent --.

Claim 3, column 6, line 12, reads "wherein R is" and should read -- wherein $R_2$ is --.

Claim 12, column 6, line 29 reads "2-(0-glycyl)glycolate" [where 0 is the numeral 0] and should read -- 2-(O-glycyl)glycolate -- [where O is the letter O].

Signed and Sealed this

Sixth Day of April, 1993

Attest:

STEPHEN G. KUNIN

*Attesting Officer*     *Acting Commissioner of Patents and Trademarks*